United States Patent [19]

Carr

[11] Patent Number: 4,808,165

[45] Date of Patent: Feb. 28, 1989

[54] INFLATION/DEFLATION DEVICE FOR BALLOON CATHETER

[76] Inventor: Ann M. Carr, 2224 NE. 9th St., Ocala, Fla. 32670

[21] Appl. No.: 92,591

[22] Filed: Sep. 3, 1987

[51] Int. Cl.$^4$ ............................................. A61M 29/02
[52] U.S. Cl. ........................................ 604/97; 128/344
[58] Field of Search ............... 128/325, 344, 348.1; 604/97, 99, 131, 151, 223, 228, 233, 218, 73–75, 181

[56] References Cited

U.S. PATENT DOCUMENTS

| 530,187 | 12/1894 | Laskey | 604/223 |
|---|---|---|---|
| 901,567 | 10/1908 | Utschig | 604/223 |
| 1,863,930 | 6/1932 | McKesson | 604/151 |
| 2,074,401 | 3/1937 | Kauzal | 604/223 |
| 3,841,331 | 10/1974 | Wilder et al. | 128/278 |
| 3,905,365 | 9/1975 | Colombo | 604/223 X |
| 4,139,008 | 2/1979 | Wagner | 128/215 |
| 4,292,974 | 10/1981 | Fogarty et al. | 128/344 |
| 4,370,982 | 2/1983 | Reilly | 604/98 |
| 4,429,724 | 2/1984 | Dorros et al. | 128/344 X |
| 4,439,185 | 3/1984 | Lundquist | 604/97 |
| 4,614,188 | 9/1986 | Bazell et al. | 128/348 |
| 4,655,749 | 4/1987 | Fischione | 604/98 |
| 4,687,472 | 8/1987 | Gross | 604/223 |

Primary Examiner—Dalton L. Truluck
Attorney, Agent, or Firm—Nixon & Vanderhye

[57] ABSTRACT

An inflation/deflation device for balloon catheter includes a pair of members pivoted to one another at one end. The first member has a recess and slot opening to one side for receiving the barrel of a syringe and the flange on the barrel, respectively. The second member carries a fitting having a slot opening to one side for receiving the flange of the plunger. The device has handles on the ends of the members remote from the pivot axis whereby the members can be moved toward and away from one another. In this manner, the balloon catheter may be inflated and deflated rapidly and with a force-multiplying effect.

15 Claims, 2 Drawing Sheets

INFLATION/DEFLATION DEVICE FOR BALLOON CATHETER

BACKGROUND AND SUMMARY OF THE INVENTION

The present invention relates generally to an inflation/deflation device for a balloon catheter used in the treatment of vascular obstructive lesions and particularly relates to an inflation/deflation device for percutaneous transluminal balloon valvuloplasty.

Catheter techniques for percutaneous transluminal treatment of vascular obstructive lesions have been used in the past. Balloon angioplasty of the peripheral vessels was subsequently introduced and extended to treatment of coronary artery obstructions. This technique was subsequently further extended to treatment of certain congenital heart lesions, including pulmonary valve stenosis, coarctation of the aorta, peripheral pulmonary artery stenosis, aortic stenosis and other stenotic or obstructive lesions.

Generally, in percutaneous transluminal balloon valvuloplasty, a balloon catheter is introduced over a guidewire into the area of the valvular obstruction. More specifically, by using radio-opaque markers indicative of the proximal and distal limits of the balloon, the balloon may be located substantially medially of the valve. The balloon is then inflated, usually with a dilute contrast medium, for a predetermined period of time to apply a controlled radial force to the balloon to open the valve, i.e., rupture the obstructive lesion about the valve. The balloon is then deflated. The process of inflation and deflation is repeated several times.

In the course of inflating the balloon catheter with the fluid, substantial pressures are necessary to open or rupture the obstructive material about the valve. For example, pressures on the order of 80-120 psi and higher may be necessary to effect opening of the valve. In conventional balloon valvuloplasty, the proximal end of the catheter is coupled to a syringe containing the inflating fluid. In most instances, the syringe is manually manipulated to inflate and deflate the balloon. However, it has been found to be physically difficult and exhausting to inflate the balloon to the desired pressure, to maintain that pressure over a predetermined period of time, and repeat that procedure several times. Substantial physical strength is required and not all individuals have the required strength to perform this function.

This problem has been addressed in U.S. Pat. No. 4,655,749. However, the device of that patent uses a drive screw fixed to a piston to effect displacement of the plunger of the syringe. Rapid inflation and deflation, therefore, cannot be effected with this device. In essence, that device simply substituted a screw drive for the conventional manual push/pull action on the plunger of a syringe, with little regard to the quick manipulation required necessary to effect rapid inflation and deflation of the balloon.

According to the present invention, there is provided a novel and improved inflation/deflation device for a balloon catheter which affords sufficient mechanical advantage or leverage to enable rapid and manual inflation and deflation of the balloon. To accomplish this, the balloon catheter is attached to a syringe in a conventional manner by using extension tubing, the syringe previously being filled with dilute contrast fluid. The syringe is then placed in the inflation/deflation device of the present invention. Particularly, that device includes a pair of elongated members or levers, one of which has an angled end portion extending toward the other member for pivotal connection therewith. The first member with the angled end portion has a central linear portion in which there is provided a recess opening laterally through one side of the member in the direction of the pivotal axis. The recess is further defined by a slot, similarly opening laterally to the same side of the device, for receiving the flange formed on the open end of the barrel of the syringe which receives the plunger. The second member is substantially linear throughout its full length and has a central slot for mounting an extension of a fitting. The fitting lies between the members and has a slot which opens laterally to the same side of the device as the slot of the first member. With this arrangement, the device as the slot of the first member. The syringe may be placed in the inflation device by engaging the conventional flanges of the syringe barrel and its plunger in the respective slots of the first and second members.

End portions of the first and second members opposite their pivotal connection one to the other constitute handles, whereby the members may be pivoted toward and away from one another. It will be appreciated that such pivoting action causes the plunger to be axially displaced into and withdrawn from the barrel. With the location of the syringe intermediate the opposite ends of the first and second members, and recognizing that the handles by which the members are moved toward and away from one another are located at the end of the device opposite the pivotal connection, substantial leverage or mechanical advantage is obtained. This leverage has a force multiplying effect, enabling the rapid pivoting of the members toward one another to inflate the balloon to the required pressure with substantially much less force than required when the plunger of the syringe is directly manually operated. Likewise, substantial leverage is obtained when moving the members away from one another to suction the syringe to rapidly deflate the balloon. Thus, the strength required for manual operation of the inflation/deflation device is minimized because of this lever-type action. Also, this arrangement enables rapid inflation and deflation of the balloon, minimizes the effect of any variability introduced by the strength of individual operators, and also decreases the time required for the procedure, thus increasing the safety of the procedure for the patient.

It is another feature of the present invention that the inflation/deflation device has a limit or stop which permits the members to be pivoted away from one another only to a predetermined extent. That extent is less than necessary to completely withdraw the plunger of the syringe from the syringe barrel. Thus, the plunger may not be inadvertently pulled out of the barrel of the syringe. The limit or stop is adjustable to accommodate different sizes of syringes.

Accordingly, it is a primary object of the present invention to provide a novel and improved inflation/deflation device for a balloon catheter particularly useful for percutaneous transluminal balloon angioplasty or valvuloplasty which minimizes or eliminates the need for substantial strength in operating the device, yet enables an individual operating the device to obtain and maintain the high balloon pressures necessary to open the obstructed site.

It is another object of the present invention to provided a novel and improved inflation/deflation device for a balloon catheter which enables rapid inflation and deflation of the balloon, and minimizes the time required for the procedure, while enhancing the safety of the procedure.

According to a preferred embodiment of the invention, there is provided a inflation/deflation device for a catheter having an inflatable balloon at its distal end and a syringe at its proximal end, the syringe including a cylindrical barrel with an open end and a plunger received within the barrel through its open end, comprising first and second elonated members connected one to the other adjacent corresponding end portions thereof for pivotal movement toward and away from one another about an axis. Means are carried by the first and second members for mounting the barrel and the plunger of the syringe, respectively, at a location spaced from the pivotal connection, the members being pivotal toward and away from one another about the axis to displace the plunger axially relative to the barrel to thereby inflate and deflate the balloon. Preferably, both the barrel mounting means and the plunger mounting means include means defining recesses opening to one side of the members, generally in the direction of the axis of the pivotal connection, for receiving the flanges of the barrel and plunger, respectively, thereby facilitating ready mounting of the syringe to the inflation/deflation device.

The invention consists in the novel parts, constructions, arrangements, combinations and improvements shown and described. The accompanying drawings, which are incorporated in and constitute a part of this specification, illustrate one embodiment of the invention and, together with the description, serve to explain the principles of the invention.

BRIEF DESCRIPTION OF THE DRAWING FIGURES

DETAILED DESCRIPTION OF THE DRAWING FIGURES

Reference will now be made in detail to the present preferred embodiment of the invention, an example of which is illustrated in the accompanying drawings.

Figure 1:
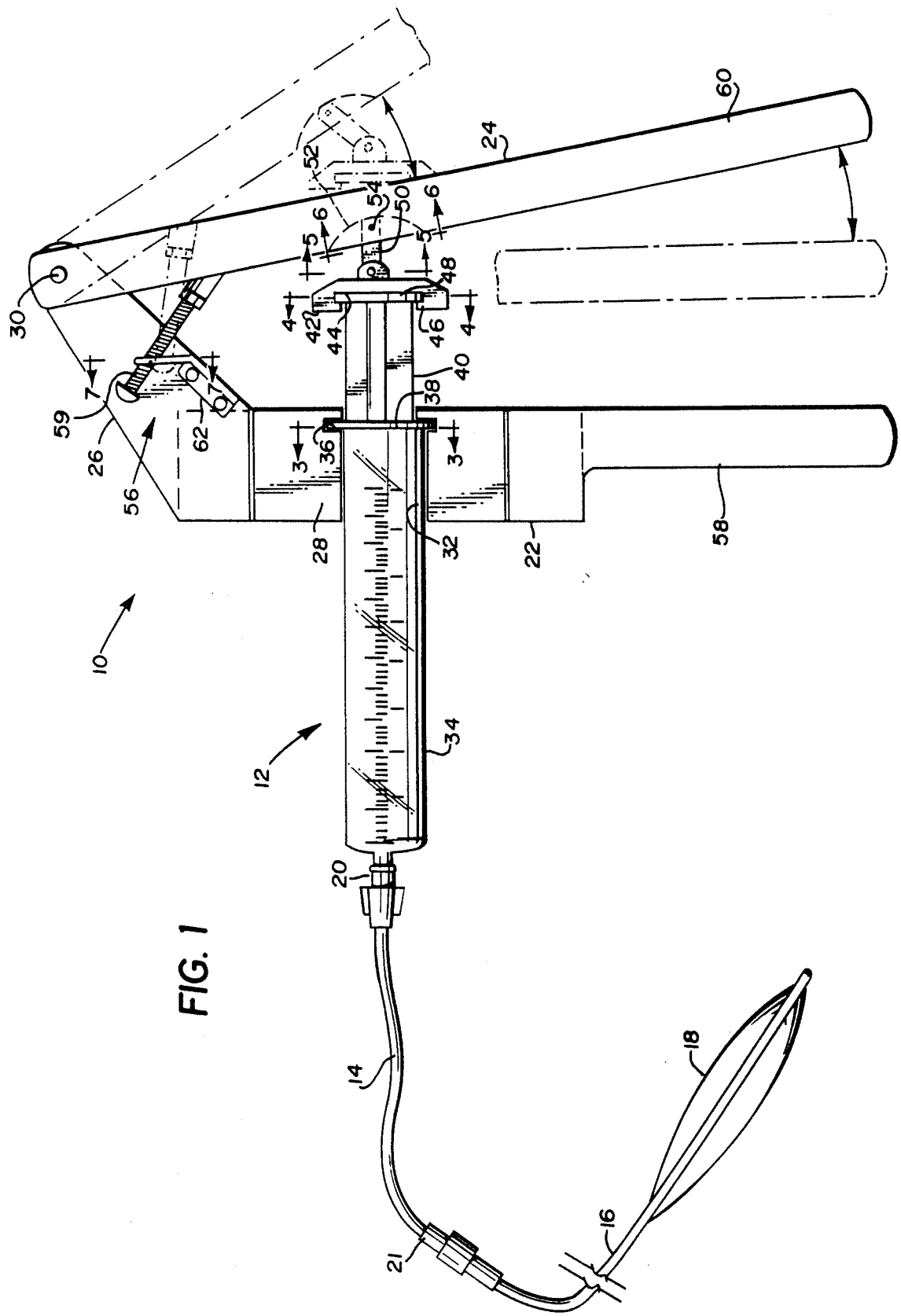
FIG. 1 is a side elevational view of an inflation/deflation device for a balloon catheter constructed in accordance with the present invention.
Figure 2:
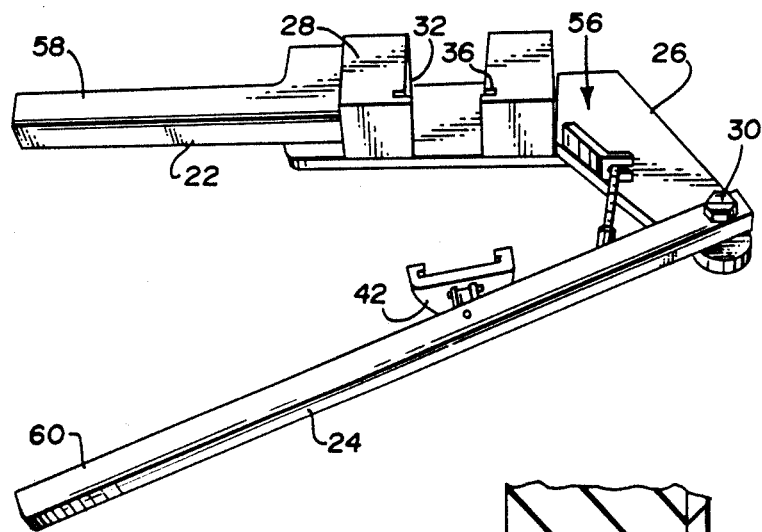
FIG. 2 is a perspective view of the device hereof on a reduced scale.
Figure 3:
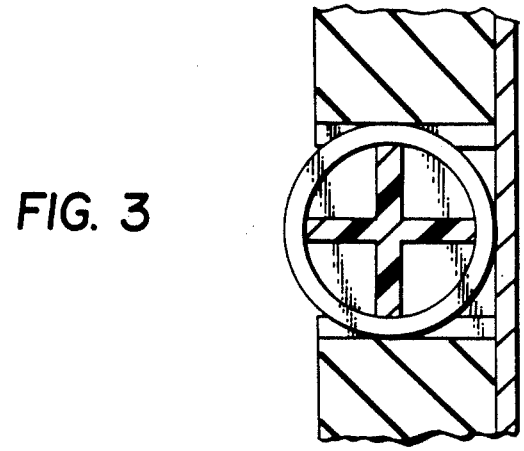
FIGS. 3-7 are fragmentary enlarged cross sectional views of the device illustrated in FIG. 1 taken generally about on lines 3—3, 4—4, 5-5, 6—6 and 7—7, respectively, in FIG. 1.
Figure 4:
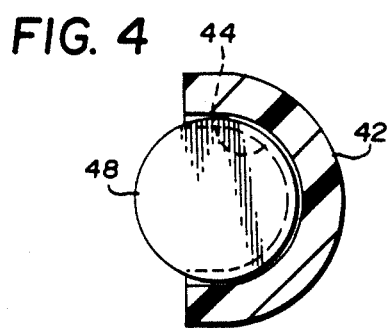

Referring now to the drawing figures, particularly to FIG. 1, there is illustrated an inflation/deflation device constructed in accordance with the present invention and generally designated 10. Device 10 mounts a syringe, generally designated 12, connected, through extension tubing 14, to the proximal end of a balloon catheter 16 having a balloon 18 adjacent its distal end. It will be appreciated that syringe 12, extension tubing 14, balloon catheter 16, and balloon 18 are of conventional construction. Suffice to say that the catheter 16 has an axial passage therethrough, enabling insertion of the catheter over a guidewire, not shown, previously disposed in and through the obstructed site for locating balloon 18. The catheter has additional passages, not shown, for conveying fluid between syringe 12 and the interior of balloon 18, whereby it may be inflated or deflated. Pressure tubing 14 has a male end which is connected to the luer lok fitting 20 of the syringe and has a female end 21 for connection with the hub of the catheter 16. Consequently, fluid may be transmitted between syringe 12 and balloon 18 through the tubing 14 and catheter 16, all in a conventional manner.

The inflation/deflation device 10 includes first and second elongated members or levers 22 and 24, respectively. First member 22 has an end portion 26 which is angled away from the generally linear extending central portion 28 of the first member and toward the second member 24. End portion 26 terminates in a pivotal connection with an end of the second member 24, the connection comprising a pin 30 extending through both members 22 and 24.

In accordance with the present invention, the syringe 12 is mounted intermediate the opposite ends of the first and second members 22 and 24. To accomplish this, the central portion 28 of the first member 22 is provided with a recess 32 intermediate its ends of receiving the body of the barrel 34 of syringe 12. Recess 32 opens laterally to one side of the inflation/deflation device 10 generally in the direction of the pivotal axis 30. The walls of member 22 defining recess 32 are also provided with opposed slots 36, likewise opening laterally to the one side of device 10, for receiving the flange 38 formed on and adjacent the end of the barrel 34 which receives plunger 40. Thus, the barrel of the syringe may be disposed laterally into recess 32 with its flange 38 engaging in the slots 36 on opposite sides of the recess. The slots 36 and flange 38 cooperate one with the other to prevent axial displacement of the barrel relative to the inflation/deflation device 10.

Figure 5:
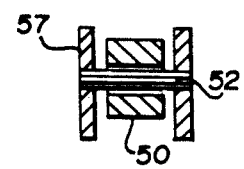
Figure 6:
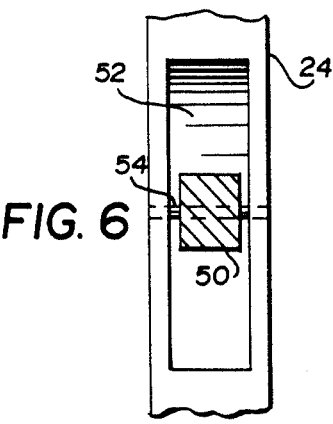
Figure 7:
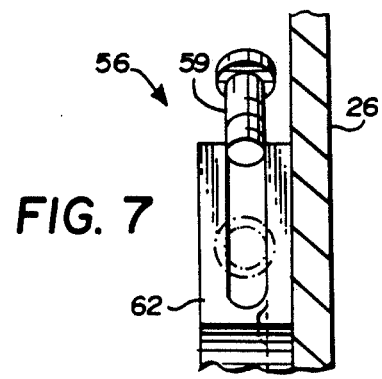

A fitting 42 is provided between members 22 and 24 and is attached to the second member 24 for connecting with the plunger of the syringe. Fitting 42 is in the form of a cap or cup having a recess or slot 44 which opens to the same side of device 10 as recess 32. The slot 44 extends below a flange 46. In this manner, the flange 48 carried by the plunger 40 may be disposed laterally into slot 44 with the flange 48 thus being captured below the flange 46 of the fitting 42. Fitting 42 is pivotally connected to member 24 by a pin 50 which extends into a slot 52 carried by member 24. Crosspin 54 pivotally secures pin 50 to member 24 in slot 52. Pin 50 is also pivoted at its opposite end to fitting 42 by a pin 52 extending laterally through pin 50 between a pair of ribs 56 on the backside of fitting 42 (FIG. 5).

The ends of members 22 and 24 opposite or remote from pivot 30 constitute handles 58 and 60, respectively. It will be appreciated that with the foregoing described arrangement of device 10, when the barrel and plunger of the syringe are captured by the first and second members 22 and 24, respectively, pivotal movement of members 22 and 24 toward and away from one another by working the handles extends and retracts, respectively, plunger 40 into and out of the barrel 34 of syringe 12. Thus, fluid within the syringe 12 may be pumped under pressure from syringe 12 through tubing 14, catheter 16 and into the balloon 18 and returned, upon withdrawal of the plunger relative to the barrel, from balloon 18 through catheter 16 and tubing 14 to the barrel of the syringe 12.

In a preferred embodiment of the present invention, there is provided a limiter, generally designated 56, for precluding movement of members 22 and 24 away from one another about pivot axis 30 to an extent sufficient to withdraw the plunger 40 from barrel 34. In a preferred form hereof, limiter 56 includes a screw 59 threaded into a threaded opening along the inside face of member 24 and extending along one side of end portion 26. A stop 62 is mounted, preferably by screw threads, on the same side of end portion 26. Stop 62 includes a pair of projections defining a slot through which the shank of screw 59 projects. Thus, upon predetermined movement of member 24 away from member 22, the head of the screw will engage the projections and prevent further pivotal movement of members 22 and 24 away from one another.

In use, the syringe is first filled with a specified amount of the dilute contrast fluid. The male end of extension tubing 14 is connected to the luer lok fitting of the syringe and the tubing is flushed with the solution. The female end of the tubing 14 is connected to the hub of catheter 16. With the syringe and catheter thus prepared, the syringe is located in the inflation/deflation device 10. Particularly, syringe 12 is inserted laterally into device 10 such that the flange 38 of barrel 34 and flange 48 of plunger 40 are disposed in the respective slots 36 and 44 of the member 22 and fitting 42 carried by member 24. The barrel 34 is thus located within recess 32 and maintained against axial displacement relative to member 22.

The catheter balloon is now ready to be prepared for the procedure. Particularly, the balloon is filled with the dilute contrast fluid by manually displacing the members 22 and 24 toward one another about pivot axis 30 by means of handles 58 and 60. The balloon is then deflated by applying negative pressure. This is accomplished by grasping handles 58 and 60 and moving members 22 and 24 away from one another to withdraw plunger 40 relative to barrel 34. The stop, however, precludes movement of member 24 relative to member 22 beyond a point which would cause extraction of plunger 40 relative to barrel 34. These inflation and deflation steps are conducted repeatedly until there is no visible air in the balloon upon inflation of the balloon.

The catheter is then placed on the guidewire and introduced transluminally to locate opposite end portions of the balloon on opposite sides of the obstructed valve or site. When properly located as determined fluoroscopically, balloon 18 is inflated by displacing member 22 and 24 toward one another to pressurize the fluid within the syringe and thus pump such fluid to inflate the balloon. After a predetermined time, a negative pressure is applied to the balloon by displacing members 22 and 24 away from one another whereby the balloon is deflated. This procedure is repeated sufficiently until the valve is opened. When the procedure is completed, negative pressure is applied to the syringe to deflate the balloon by moving the members 22 and 24 away from one another whereby the catheter may be withdrawn from the site.

It will be appreciated that a pressure measuring device may be disposed between the syringe and the catheter if pressure measurement is required as in pulmonary valvuloplasty. Thus, the male fitting on a conventional pressure gauge would be attached to the luer lok tip of the syringe and the male end of the pressure tubing would be attached to the pressure gauge. Thus, pressure readings may be obtained throughout the manipulation of the members 22 and 24 during inflation and deflation of the balloon.

It will thus be appreciated that the objects of the present invention are fully accomplished in that there has been provided an inflation/deflation device for a balloon catheter wherein substantial pressures may be provided the balloon with minimum manual force applied to the device. This is accomplished through the leverage or mechanical advantage obtained by manipulating the handles of the device with the syringe located intermediate the handles and the pivotal connection between the handles. Additionally, the device is readily and easily used, particularly by enabling quick assembly of the syringe into the device. It may also be safely used by the provision of the limiter or stop which prohibits withdrawal of the plunger of the syringe from its barrel.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An inflation/deflation device for a catheter having an inflatable balloon at its distal end and a syringe at its proximal end, the syringe including a cylindrical barrel and plunger received within the barrel, comprising:

first and second elongated members connected one to the other adjacent corresponding end portions thereof for pivotal movement toward and away from one another about an axis;

means carried by said first member for fixedly mounting the barrel of the syringe relative to said first member against axial displacement of the barrel relative to the first member at a location therealong spaced from said pivotal connection, said barrel mounting means including means defining a slot opening laterally to one side of said device and said first member generally in the direction of the axis of said pivotal connection for receiving a flange formed about the barrel; and means carried by said second member for fixedly mounting the plunger of the syringe relative to said second member against axial displacement of the plunger relative to the second member at a location therealong spaced from said pivotal connection, said plunger mounting means including means defining a slot opening laterally to said one side of said device and said second member generally in the direction of the axis of said pivotal connection for receiving a flange formed about the plunger;

said slots enabling the syringe to be received and mounted on said device and removed therefrom from said one side of the device;

said members being pivotal toward and away from one another about said axis to positively displace the plunger axially relative to the barrel in opposite directions to thereby positively inflate and positively deflate the balloon, respectively, in response to said pivotal movement.

2. The device according to claim 1 and means cooperable between said slot defining means and said second member enabling pivotal movement of said slot defining means relative to said second member in response to pivotal movement of said members relative to one another.

3. The device according to claim 1 wherein said barrel mounting means and said plunger mounting means are carried by said first and second members, respectively, intermediate their ends, the ends of said members opposite the pivotal connection therebetween constituting handles for pivoting said members toward and away from one another.

4. The device according to claim 1 including means carried by said members independent of the plunger and barrel and cooperable solely between said members to limit pivotal movement of said members in a direction away from one another.

5. The device according to claim 4 wherein said limiting means is adjustable thereby to enable adjustment of the extent of the pivotal movement of said members away from one another.

6. The device according to claim 1 wherein one of said first and second members includes first and second portions angularly related one to the other in a plane normal to said axis with said first portion extending from said second portion in a direction toward the other of said first and second members and mounting said pivotal connection.

7. The device according to claim 1 in combination with said catheter, said balloon and said syringe.

8. An inflation/deflation device for a catheter having an inflatable balloon at its distal end and a syringe at its proximal end, the syringe including a cylindrical barrel and a plunger received within the barrel, comprising:

first and second elongated members connected one to the other for movement toward and away from one another;

means carried by said first member intermediate its ends including means defining a recess opening laterally to one side of said first member for receiving the barrel of the syringe and fixedly mounting said barrel against axial displacement relative to said first member; and means carried by said second member intermediate its ends including means defining a recess opening laterally to one side of said member for receiving the plunger of the syringe and fixedly mounting said plunger against axial displacement relative to said second member;

said recesses enabling the syringe to be received and mounted on said device and removed therefrom from said one side of the device;

said members being movable toward and away from one another to positively displace the plunger axially relative to the barrel in opposite directions to thereby positively inflate and positively deflate the balloon, respectively, in response to said movement.

9. The device according to claim 8 including means cooperable between said plunger mounting means and said second member enabling pivotal movement of said plunger mounting means relative to said second member in response to pivotal movement of said members relative to one another.

10. The device according to claim 8 wherein said recess defining means of each said first and second members define slots for receiving respective flanges formed on an end of the barrel and an end of the plunger thereby to enable position axial movement of the plunger relative to the barrel in opposite directions response to movement of said members.

11. The device according to claim 10 wherein said first and second elongated members are connected one to the other adjacent corresponding end portions thereof for pivotal movement toward and away from one another about an axis, said barrel receiving and mounting means and said plunger receiving and mounting means being carried by said first and second members, respectively, intermediate their ends, the ends of said members opposite the pivotal connection therebetween constituting handles for pivoting said members toward and away from one another.

12. The device according to claim 11, including means carried by said members independent of the plunger and barrel and cooperable solely between said members to limit pivotal movement of said members in a direction away from one another, said limiting means being adjustable thereby to enable adjustment of the extent of the pivotal movement of said members away from one another.

13. The device according to claim 8 and means cooperable between said recess defining means and said second member enabling pivotal movement of said recess defining means relative to said second member in response to pivotal movement of said members relative to one another.

14. The device according to claim 11 and means cooperable between said recess defining means and said second member enabling pivotal movement of said recess defining means relative to said second member in response to pivotal movement of said members relative to one another.

15. The device according to claim 12 and means cooperable between said recess defining means and said second member enabling pivotal movement of said recess defining means relative to said second member in response to pivotal movement of said members relative to one another.

* * * * *